US006009180A

United States Patent [19]

Andersson

[11] Patent Number: 6,009,180

[45] **Date of Patent: *Dec. 28, 1999**

[54] FLUIDIC ELEMENT NOISE AND VIBRATION CONTROL CONSTRUCTS AND METHODS

[75] Inventor: Anders O. Andersson, Seattle, Wash.

[73] Assignee: The Boeing Company, Seattle, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/710,352

[22] Filed: Sep. 17, 1996

[51] Int. Cl.[6] .................................................... A61F 11/06

[52] U.S. Cl. .......................................... 381/71.4; 381/71.7

[58] Field of Search ................................. 381/71.1, 71.2, 381/71.4, 71.5, 71.7; 248/635, 550; 267/136; 181/206, 224, 220

[56] References Cited

U.S. PATENT DOCUMENTS 4,091,892 5/1978 Hehmann et al. .
4,747,467 5/1988 Lyon et al. .
5,374,025 12/1994 Whelpley et al. ...................... 248/550

*Primary Examiner*—Vivian Chang
*Attorney, Agent, or Firm*—Christensen O'Connor Johnson & Kindness PLLC

[57] ABSTRACT

Fluidic constructs, including grouped stacks of fluidic elements, that provide countersound to control sound in a noisy environment, prevent radiation of sound from vibrating surfaces, reduce sound-induced vibration of surfaces, and absorb sound that might otherwise impact on surfaces, are provided. These constructs may have a wide range of geometries for specific applications, but generally include a face plate on one side, and a back plate on the other side. Supply ports on the back plate provide a supply of fluid that flows through the construct, while undergoing acoustic modulation through fluidic amplifiers. The face plate includes input ports that sense sound waves to be controlled, and transmits this sound to influence the acoustic modulation of the supplied fluid. The construct produces an amplified output, having sound out of phase with the sound sensed by the input ports, at output ports on the face plate in a sufficient volume to substantially neutralize incoming sound waves, or reduce sound radiation from an object. Any sound produced by the construct of the invention that is substantially in phase with sound to be neutralized is dumped at a sufficient distance from the produced countersound to minimize interference.

13 Claims, 11 Drawing Sheets

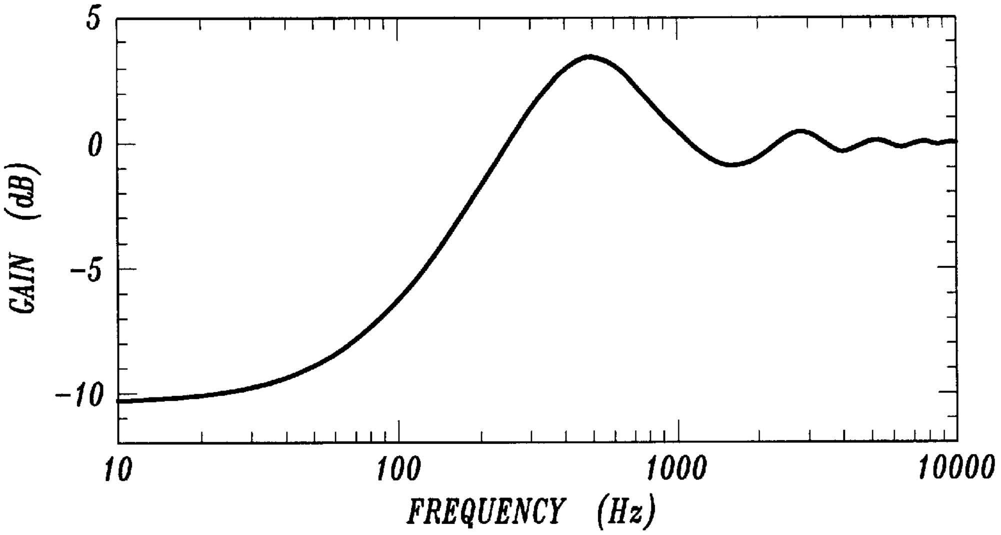
Fig. 9D
Fig. 10
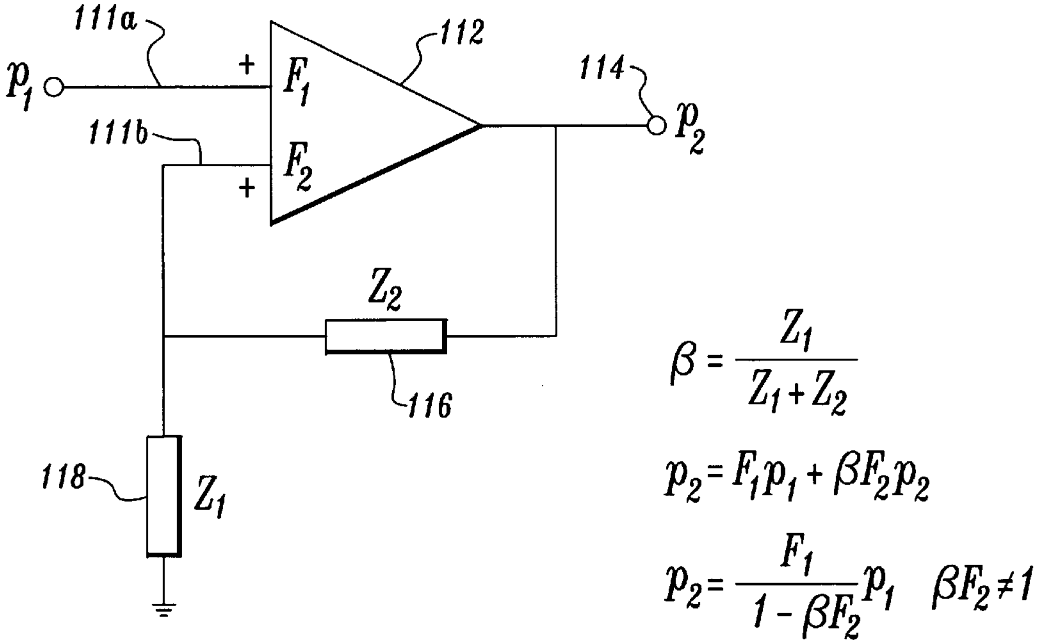
$$\beta = \frac{Z_1}{Z_1 + Z_2}$$
$$p_2 = F_1 p_1 + \beta F_2 p_2$$
$$p_2 = \frac{F_1}{1 - \beta F_2} p_1 \quad \beta F_2 \neq 1$$

FLUIDIC ELEMENT NOISE AND VIBRATION CONTROL CONSTRUCTS AND METHODS

FIELD OF THE INVENTION

The invention relates to the field of noise reduction, and provides constructs that comprise fluidic elements for controlling the impedance of the construct to attenuate sound waves over a broad range of frequencies.

BACKGROUND OF THE INVENTION

Several techniques have been developed for noise reduction. These include, for instance, the use of passive mufflers, such as those found on the exhaust systems of automobiles. Other techniques include the use of noise-reducing enclosures around the noise-creating device and sound-absorbing materials to reduce the reverberation of sound in the environment. In addition, active techniques using the generation of "counternoise" to neutralize the noise have also been demonstrated successfully. For example, a system of electrically powered microphones for detecting noise, linked to electrically powered speakers for generating a counternoise, has been used successfully in the cabin of propeller-driven aircraft. The electrical microphone-speaker system requires a plurality of these devices distributed along the walls of the cabin, and is limited to reducing noise within a narrow bandwidth. Thus, the system is well adapted for attenuating the periodic sound pressure generated by a rotating impeller, but is not well suited for reducing the broad sound wave band generated by a jet engine or the aerodynamic boundary layer of a flying aircraft.

There exists a need for a device that is able to attenuate sound waves, across a broad frequency band, that is reliable and cost-effective. Preferably, the device should not require significant input of maintenance, and should be able to operate effectively for long periods of time without continuous monitoring. Furthermore, the device should desirably be energy efficient, either not using power, or using very little power. Moreover, the device should be space-efficient, and not bulky, so that it can be readily used in a variety of applications where space limitations are important. Finally, the device should also be light weight to allow use in weight-sensitive applications, such as aircraft cabins.

SUMMARY OF THE INVENTION

The invention provides constructs of controlled, typically low, sound impedance that effectively reduce broad frequency band noise in an environment. These constructs may be fabricated in a variety of shapes, including planar shapes suitable for use as wall coverings, and cylindrical shapes suitable for use in mufflers, and other noise reduction applications. The constructs are of light weight, and are relatively thin, so that they are space efficient. Moreover, the constructs do not require an input of electrical, or another power other than an input of a suitably pressurized fluid, gaseous or liquid.

The constructs of the invention comprise an array made up of a plurality of grouped stacks of sheets having cut out fluidic elements thereon. Each of the stacks of sheets of fluidic elements includes at least one sheet, and preferably many sheets, having fluidic amplifiers. These fluidic amplifiers may be cascaded so that each of the stacks is able to amplify significantly the acoustic pressure of the fluid in contact with the stack. The fluidic construct also has at least one control port (or "microphone") in a face plate of the construct that faces the environment in which sound must be controlled. Input received in this control port modulates the fluid flow through the construct from the supply port to produce sound destructively out of phase with the sound in the environment. The amplified and out-of-phase sound ("countersound") generated is expelled from the construct through at least one output port ("speaker") and controls or reduces incident sound waves. At the same time, an unwanted portion of the amplified sound pressure is dumped, via at least one dump port of the array of fluidic elements, to a sufficiently remote location so that it does not generate significant interference with the attenuation of the sound.

Due to the travel time of the air supply through the fluidic element construct to the output port, instabilities in the fluidic circuit of the construct could occur at high frequencies. To counteract this possibility, acoustic low pass filters, in the form of orifices and volumes, are included in the construct to filter out the high frequencies.

In a preferred embodiment, the "sheets of fluidic elements" are each fabricated from relatively thin sheets of material about 0.1 mm to about 0.5 mm thick. A range of materials are useful, including metal foil, plastic sheeting, etc. Each of these sheets preferably has a plurality of fluidic elements cut out of the sheet. A multiplicity of such sheets having fluidic amplifiers, alternating with sheets having transfer elements, are grouped together into a first "stack" of elements. The transfer element on one sheet controls the flow or transmission of fluid between fluidic elements on sheets on either side of the one sheet. A plurality of these stacks of fluidic and transfer elements are then grouped together to form "an array" of stacks. Depending upon the geometry of this array, it comprises the noise control "wall paper", or cylindrical roll muffler embodiments of the invention, described in more detail below.

While constructs of the invention may be customized to particular applications and therefore come in a range of geometries, each suited to a particular application, in one embodiment described herein, the noise control construct of the invention is in the form of a "sound absorbing wall paper" that includes substantially planar fluidic elements, such as a series of sheets, arranged in a predetermined sequence to achieve the desired attenuation of noise. This noise-reducing "wall paper" may be used in a variety of applications, including the lining of the side walls of cabins of aircraft and other vehicles, use in theaters, recording studios, and opera halls to tailor acoustics, in certain manufacturing environments that generate high levels of noise that pose a hazard to health, and the like.

In another embodiment of the invention, the noise control construct is in substantially cylindrical form, with the thin sheets of fluidic elements are rolled up together like a roll of sheets of parchment. This type of construct is used as a muffler for sound in the fluid that is passing through the axial bore of the construct. In another version of the muffler embodiment, the cylindrical roll of sheets of fluidic elements is axially aligned with a cylindrical passive muffler to form a combination muffler that is highly effective for noise attenuation. In a further embodiment, the fluidic element constructs are interspersed with passive elements, either in a planar or a cylindrical arrangement. In this latter type of combined construct, the passive elements serve to increase the acoustical stability of the construct and increase its frequency range of attenuation.

The fluidic element noise control constructs of the invention may be fabricated in a variety of thicknesses, the thinner constructs being preferred. However, when used in the "wall paper" embodiment, the thickness of the construct is generally expected to be in the range from about 1.0 to about 5.0 mm. Sound waves having a frequency in the range from about 0 to about 400 Hz can be attenuated with such a construct. While it is desirable for most applications to minimize thickness and size of the fluidic elements, currently feasible technology appears to limit the thickness of the "wallpaper" to this 1.0–5.0 mm range. However, if thinner and smaller fluidic elements are feasible, then the constructs may attenuate sound waves having a frequency in the range from about 0 to about 2,000 Hz.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 9D is a graphical depiction of closed loop gain vs. frequency of the model of FIG. 9A;

FIG. 10 is a schematic representation of an embodiment of a gain-boosting circuit in accordance with the invention;

DETAILED DESCRIPTION OF THE PREFERRED EMBODIMENT

Figure 1:
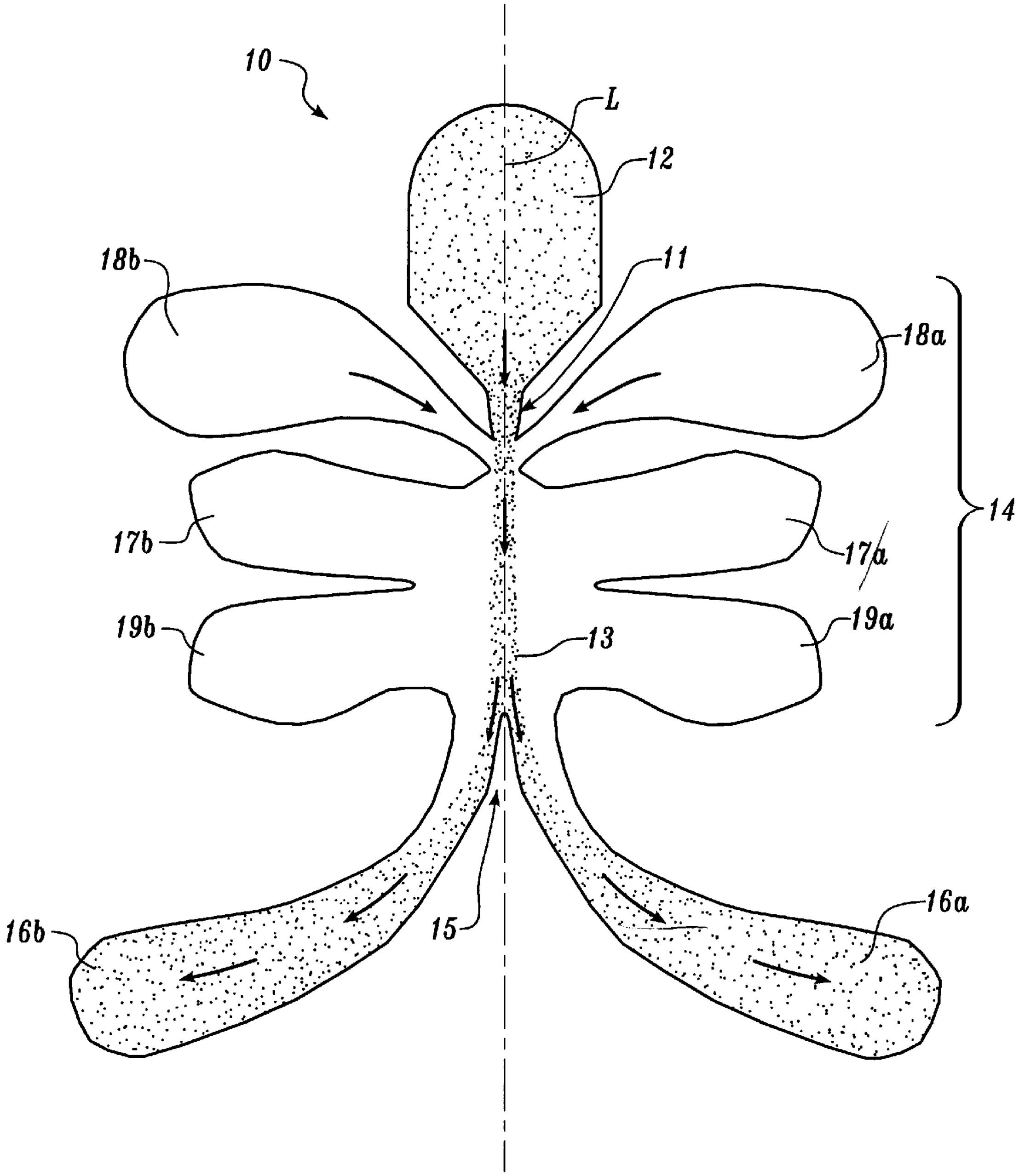
FIG. 1 is a schematic diagram of a fluidic amplifier.

The invention provides constructs that actively control sound impedance. The constructs are composed of stacks of laminated sheets that are arranged in the form of an array. Preferably, each sheet in the array contains either a fluidic element or a transfer between fluidic elements. Some of the fluidic elements are fluidic amplifiers, and these amplifiers are preferably cascaded in series. The input to the series of amplifiers is either from the side exposed to the noisy environment, and so excited by sound waves, or the side where sound radiation from an object should be controlled. The construct also receives a supply of fluid that is modulated by the input to produce a volume of "countersound" or sound out of phase with the sound to be controlled. The effect is to actively control the acoustic impedance such that an exciting sound wave is absorbed, or sound radiation from a vibrating object (such as an aircraft cabin wall) which the construct is shielding, is minimized.

It is a unique aspect of the invention that it uses fluidics as the medium for providing the cancellation of sound waves (noise) and thereby allows the use of potentially the entire surfaces of walls and other objects, as "speakers" for canceling these noise vibrations using input from "microphones" in surfaces exposed to the noise.

The definitions that follow are not intended to override the usual understanding of the meanings of these terms in the art but to clarify the terms to facilitate understanding of the invention. In the specification and claims, the tern "substantially planar" is intended to include constructs that have a large radius of curvature, such as wall coverings for the side walls of an aircraft which has a cylindrical fuselage. The tern "sheet," as used in the specification and claims, means a sheet fabricated from a material suitable for use in making fluidic elements and transfer elements, such as organic polymer (plastic), metal foil, and the like. Preferably, the sheets used to produce the fluidic constructs of the invention are as thin as possible for least mass. Typically, sheets are in the thickness range from about 0.2 to about 0.5 millimeters, although they may be as thin as 0.05 millimeters, and thickness may range upward, depending upon the specific application. A "fluidic element" is a precisely shaped cut-out section of a sheet that has at least an input point to receive fluid and an output point from which fluid is discharged. While the sizes of the cut-out fluidic elements will vary depending upon the specific application of the fluidic construct, the elements may typically be in the size range of about 5 mm to 50 mm square. A multiplicity of small cut-out elements in each sheet of an array makes up a "wallpaper" type of construct. A "fluidic amplifier" is a fluidic element that amplifies acoustic pressure of a supplied fluid. A "transfer element" is also in a generic sense a fluidic element, but it generally does not amplify and it is interposed, usually on a sheet between a first and second sheet, to control fluid communication from a fluidic element on the first sheet to a fluidic element on the second sheet. The term "stack" relating to fluidic elements means the repeating unit of a group of sheets containing fluidic elements stacked one atop the other, usually with transfer elements interposed between to control fluid flow. The term "array of stacks" or "array of stacks of fluidic elements" means a series of stacks of fluidic elements grouped together and in fluid communication. Typically, stacks are compiled into a fluidic construct for noise reduction, in accordance with the invention. Generally, an array of fluidic elements will include several stacks, each of which has at least one, and preferably several, fluidic amplifiers. A "vent" is an area in an element of a sheet, such as part of the body of a fluidic amplifier, where pressure is kept at ambient levels. A "face plate" is the top sheet of an acoustic fluidic array, where the "microphone" (input or control port) and the "loudspeaker" (output port) openings are located. A "back plate" is the rear sheet of an acoustic fluidic array, where the dump ports (or dump openings) are located.

It is one of the objectives of the invention to create a desirable acoustic impedance. For a wall absorber in a room, this may be a resistive impedance in the range 1–2 ρc (where ρ is the air density, and c is the speed of sound), and for a muffler an impedance proportional to (1.8–1.5j) ω over some frequency range in order to effectively suppress the least attenuated mode (where $j=\sqrt{-1}$, and ω=circular frequency). For a vibrating wall, the optimal impedance would be zero in order to completely suppress radiation. It is desired to create an impedance in the range 0.5–1.0 ρc over the frequency range where excessive noise exists, or to create a very low impedance, of the order of 0.1 ρc, at some discrete frequency or frequencies.

The general concept may better be understood with reference to a specific example. Thus, consider a wall lining that consists of an array of fluidic and transfer elements. The fluidic elements are arranged so that the control port of the first amplifier stage ("microphone"), and the output port of the last amplifier stage ("speaker"), are both exposed to an incident wave. The ports are arranged in such a way that a positive pressure at the control port causes a negative pressure (or "counternoise") at the output port, thus counteracting the incident wave. Due to the time delay of the response of the output port, the counternoise may only arrive in time for frequencies that are lower than a limiting frequency, defined below, while for frequencies higher than the limiting frequency, the damping in the circuit must be sufficiently large to prevent self-excited oscillations. The limiting frequency, f, is set by the accumulated time delay, d, through the fluidic circuit (i.e., from control port to output port). At this frequency, the time delay corresponds to a phase shift of about 60° to about 90°, i.e., $\pi/3<fd<\pi/2$. At a frequency where fd equals π, the gain around the circuit, closed over the microphone and loudspeaker openings, must be less than 1.0 in order to avoid the occurrence of self-excited oscillations. This requirement is fulfilled by insertion of acoustic filters, in the form of resistive orifices or capillaries, and volumes, in the circuit. However, these filters further reduce the upper frequency range at which the circuit is effective.

The invention may be better understood with reference to the attached drawings, not to scale, that represent certain embodiments of the invention. Clearly, the invention is not limited to the embodiments illustrated, but encompasses all of the technology that is disclosed and claimed herein, as well as variations and modifications that may become apparent to one of skill in the art who has read this disclosure.

FIG. 1 is a schematic representation of an example of a fluidic amplifier 10. Clearly, other designs are also useful. In the amplifier shown, there is a supply port 12 at one end for carrying a fluid through a throat 11 into the amplifier body 14. The amplifier body 14 flares outward from the end of throat 11 to an opposite end of the body that includes two output ports 16*a* and 16*b*. Output ports 16*a* and 16*b* are separated by a V-shaped splitter 15 at the output end of amplifier body 14, with the apex of the vee oriented directly opposite, and in line with, a line of center L (in this case L is also a line of symmetry of the amplifier 10) of supply port 12. Thus, fluid entering supply port 12, and moving through a throat 11 into the amplifier body 14 in a straight line as shown by arrows, would be split in half by the vee so that one-half would enter each of the output ports 16*a* and 16*b*. In order to control the division of the fluid pressure between output ports 16*a* and 16*b*, the amplifier illustrated has a pair of opposed control ports 18*a* and 18*b*, disposed at right angles to fluid moving in a jet 13 through the body 14 of the amplifier from the supply port 12 to the output ports 16*a*, 16*b*. Thus, by varying the pressure of control fluid entering through ports 18*a* and 18*b*, the flow of fluid through amplifier body 14 may be deflected to control the amount of fluid entering output ports 16*a* and 16*b*. As the control port (18*a*, 18*b*) pressure is controlled by an acoustic signal, the output port (16*a*, 16*b*) pressures will reflect this pressure signal, with a time delay and a pressure gain. Additionally, the exemplified amplifier 10 shown has two pairs of opposing vents 17*a*, 17*b* and 19*a*, 19*b*, located on either side of the amplifier body 14, that are at substantially ambient pressure.

Figure 2:
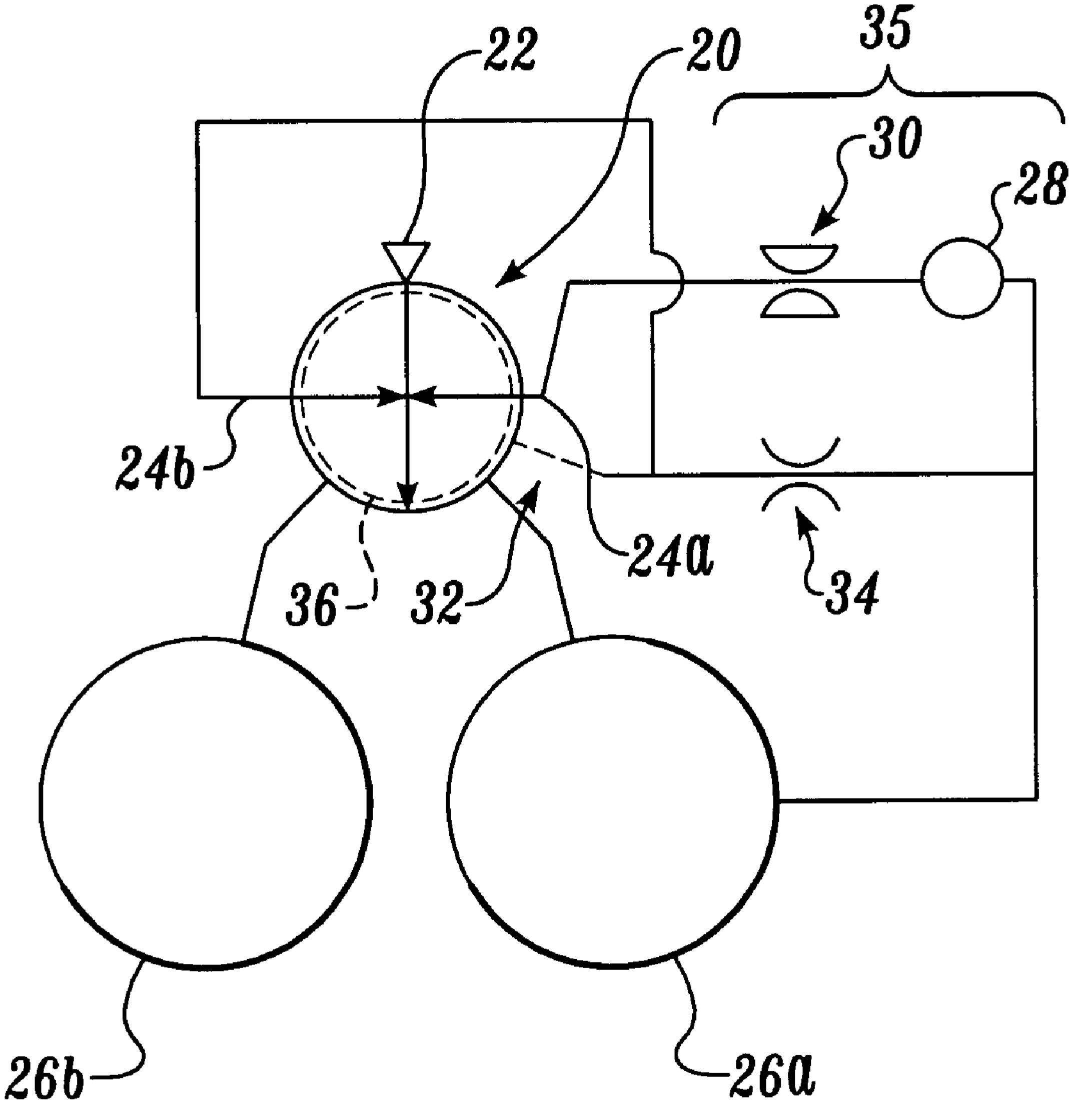
FIG. 2 is a representation of a fluidic amplifier, with two control ports, in a fluidic circuit.

In order to simplify the analysis of a series of fluidic amplifiers, mathematical relationships have been developed. Moreover, in order to simplify the illustration of fluidic amplifiers conventional illustrations have also been developed. For example, FIG. 2 illustrates an example of a proportional fluidic amplifier 20 in a simple fluidic circuit, in accordance with the invention. Air supplied to the fluidic amplifier 20 enters at supply port 22 and its acoustic modulation is controlled by fluid entering on opposite sides of the fluidic amplifier 20 through control ports 24*a* and 24*b* so that the output acoustic pressure appears amplified and reversed at output ports 26*a* and 26*b*. If this amplifier were the first stage of a multi-stage amplifier, it would be followed by another amplifier stage, with the two output ports 26*a* and 26*b* connected to the control ports of the next stage. If this is the last amplifier stage, then, in accordance with the invention, the output of the port with sound waves in phase with the first stage control port pressure is dumped at a sufficient distance from the fluidic circuit to prevent substantial interference with its function of controlling the acoustic impedance. The output of the other output port, out of phase with the sound waves at the first stage control port, is exposed to the environment where noise must be reduced. This output port is effectively the "speaker" that produces "counternoise," i.e., the out of phase sound.

The acoustic pressure to be amplified is applied to volume 28 which acts like a capacitor. The volume is connected to control port 24*a* via resistive orifice 30. The combination of volume 28 and orifice 30 acts as a low pass filter 35, i.e., at low frequencies volume 28 is pumped up and its pressure is transmitted to control port 24*a*, while at high frequencies volume 28 is emptied after a pressurization, before the pressure has time to be transmitted to control port 24*a*. In addition, the figure shows the vent 36 as a clashed circle connected by 32 and resistive orifice 34 to the environment. Resistance 34 is large enough to substantially prevent transmission of sound pressure to the vent 36.

Figure 3:
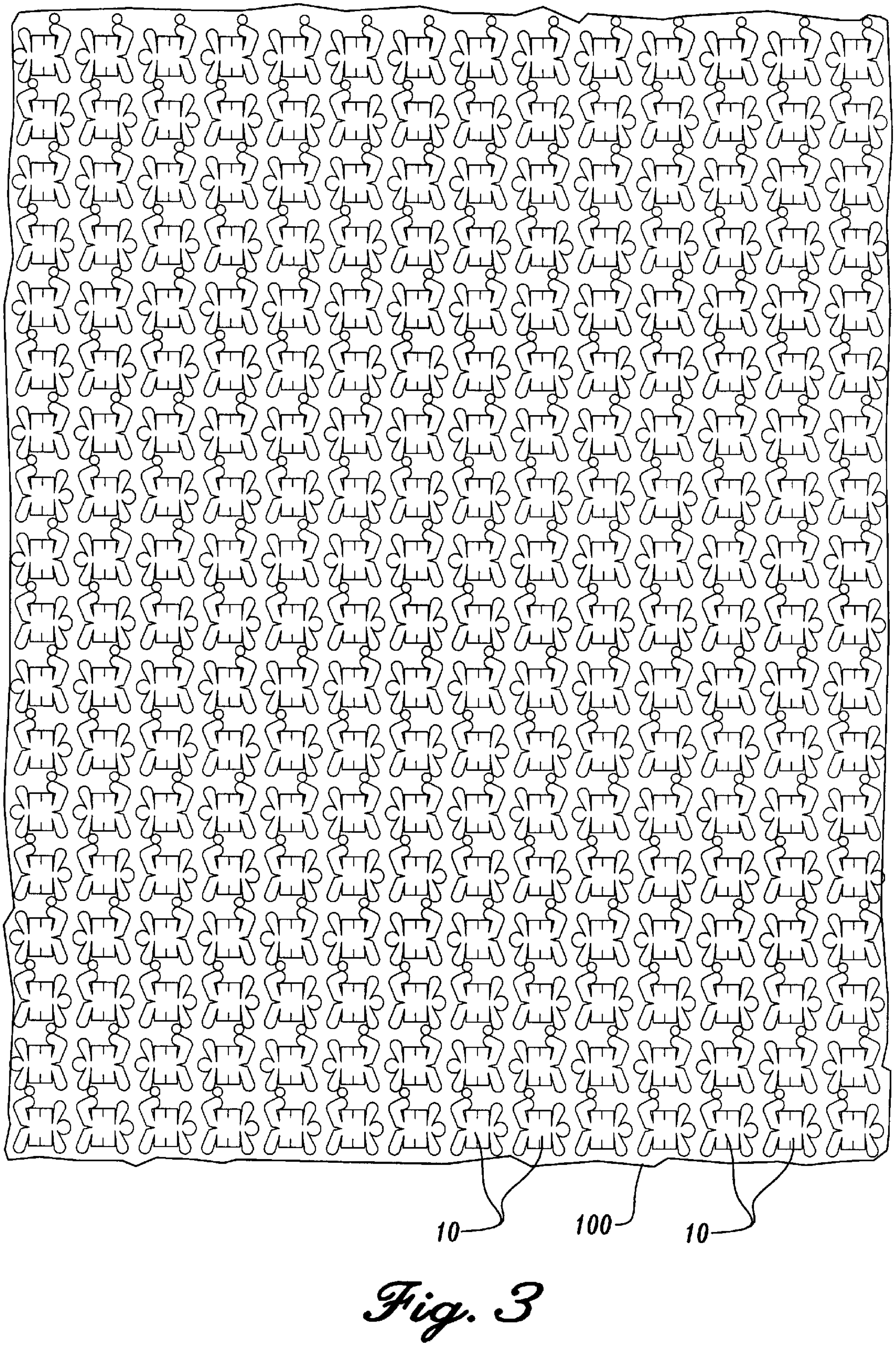
FIG. 3 is a schematic diagram of a frontal view of an embodiment of a thin sheet of fluidic elements showing a plurality of fluidic amplifiers (in this case repeating units) cut out of the sheet, in accordance with the invention.

While FIG. 1 has illustrated an apparent single fluidic element cut out of a sheet, more typically multiples of such fluidic elements will be cut out of a sheet. FIG. 3 illustrates an example of a sheet 100 having multiple cut-out fluidic elements 10, in this case fluidic amplifiers. As pointed out above, each individual cut-out fluidic element 10 may have the dimensions from about 5 mm to about 50 mm square. Consequently, a fluidic construct "wallpaper" for use in reducing or controlling the sound in an aircraft cabin would contain stacks of sheets that together have literally millions of cut-out fluidic elements. The back plate of the fluidic element construct would be equipped with supply tubes (not shown) attached to supply ports of its cut-out fluidic elements to supply the necessary fluid for operating the fluidic construct. The back plate would also be equipped with tubes to collect the fluid output from the dump ports.

Figure 4:
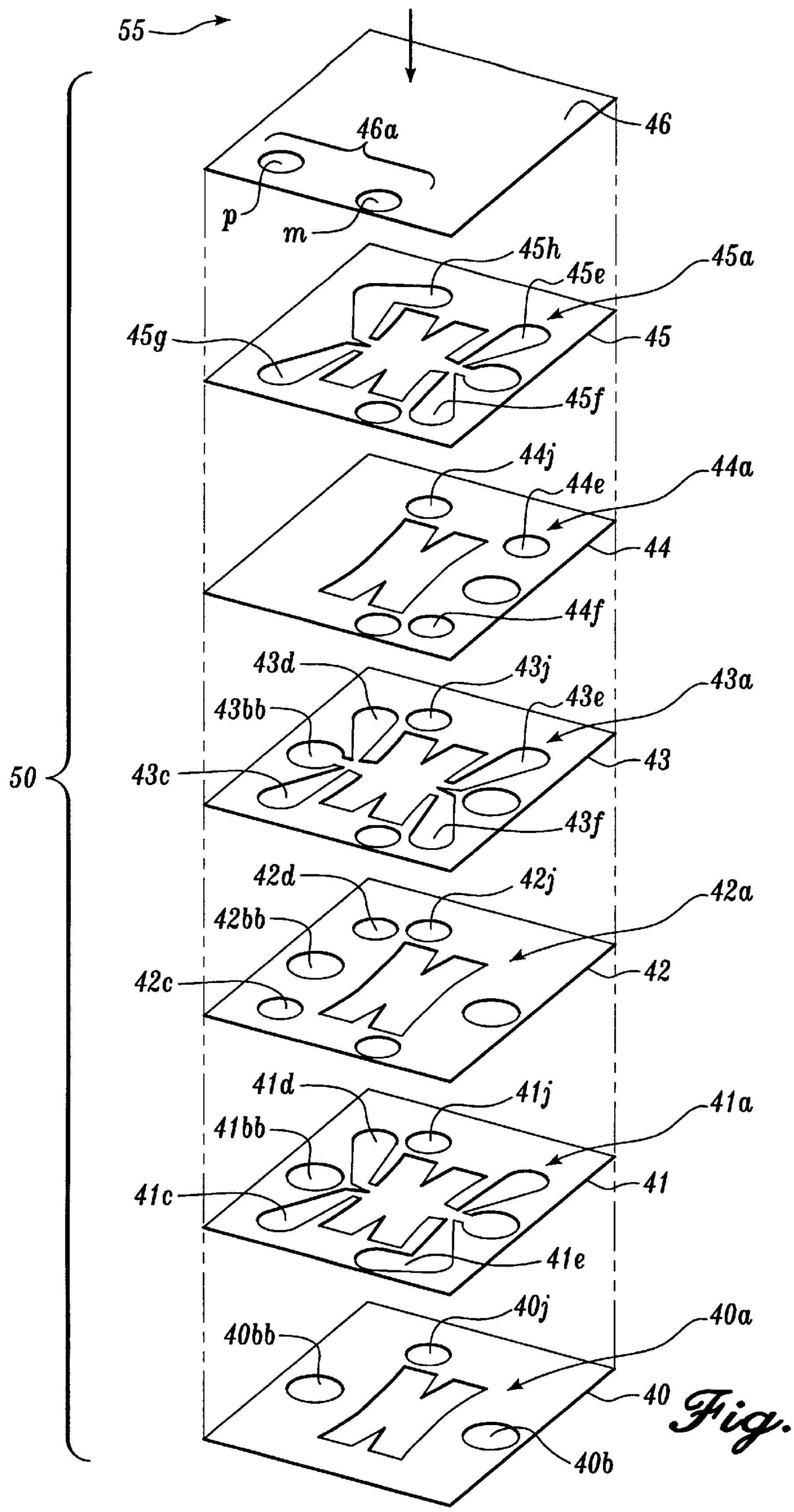
FIG. 4 is a schematic illustration of an exploded view of an embodiment of a simplified stack of sheets of the invention having fluidic elements and transfer elements.

FIG. 4 is a schematic simplified representation of an exploded view of a stack 50 consisting of a plurality of sheets of fluidic elements that may be grouped together to form a controlled impedance construct, in accordance with the invention. Typically, a plurality of stacks of sheets of fluidic elements are grouped side-by-side to form an array in order to produce a useful fluidic construct. For simplicity, each of the planar sheets 40, 41, 42, 43, 44, 45, and 46 of the stack 50 has a single cut-out fluidic element, 40*a*, 41*a*, 42*a*, 43*a*, 44*a*, 45*a*, and 46*a*, respectively, although in practice each sheet will contain many such cut-out elements, as discussed above, with reference to FIG. 3. For simplicity, each sheet in FIG. 4 will be referred to as a "fluidic element" since the sheets have one fluidic element each Also as shown, the stack 50 of planar fluidic elements 40–46 includes a supply port 40*b* in the first element 40 of the stack 50, known as the "back plate." In the event that the planar stack of elements makes up, for example, a section of an acoustic wallpaper for an aircraft cabin, then the air supply for port 40*b* may be from the air conditioning system of the aircraft. Otherwise, another convenient source may be used. The fluid supply flows into the supply port 40*b* of the fluidic element 40 and thence into the supply port of fluidic element 41 where it is divided into two outputs: 41*c* and 41*d*. The proportion of flow to each of those output ports 41*c* and 41*d* is determined by the pressure at control port 41*e* of amplifier 41*a*. Control port 41*e* is connected to "microphone" port m of face plate 46 of the fluidic stack via fluidic elements 45, 44, 43, and 42. The two output ports of element 41, 41*c* and 41*d*, are in fluid connection with the control ports 43*c* and 43*d* of the next amplifier stage 43*a*, on sheet 43, via the transfer sheet 42 (i.e., through portals 42*c* and 42*d*, respectively). Note that fluidic amplifier43 is supplied at port 43*bb* through portals 42*bb*, 41*bb*, and 40*bb*, which in turn is connected to the same supply of fluid as portal 40*b*. The output ports 43*e* and 43*f* of amplifier 43*a* are in turn in fluid connection with the control ports 45*e* and 45*f* of the final amplifier stage 45 via the transfer 44 (i.e., ports 44*e* and 44*f*, respectively). One output 45*g* (the "speaker") of the final amplifier 45*a* is connected to the environment via orifice p of face plate 46, while the other output 45*h* is dumped sequentially via orifices 44*j*, 43*j*, 42*j*, and 41*j* to dump port 40*j* of back plate element 40. As will be appreciated, the output of any stack may be successively amplified through a plurality of fluidic amplifiers before being output into the environment. The output of 45*g*, with its amplified and inverted (or "out-of-phase") acoustic pressure, then encounters the incoming sound wave, illustrated as 55, to attenuate that sound wave. It should be noted that the pressure at "microphone" port m is the residual pressure of the incoming sound wave 55 after being counteracted by the efflux from the loudspeaker port p.

Typically, the function of the first few amplification stages is to amplify the pressure, while the function of the last amplification stage is to increase the fluid flow. For this purpose, the last stage might consist of one or more amplifiers in parallel. The aim of the last stage is to match the volume velocity of the incoming sound wave.

In order to better understand this design requirement, an example will be given. Assume that a sound wave with 85 dB amplitude is normally incident on the fluidic construct. The peak particle velocity of that wave is then 0.0027 meters per second. Assume further that the steady flow through the last amplifier stage can be modulated with acoustic pulsations at ±30%. Then, this steady flow would have to be 0.009 meters per second. If the repeating-unit stack area is 0.0001 sq. meters, and the two amplifiers are used in parallel, then the volume flow through each of the last two amplifier stages is $9\times10^{-7}$ $m^3$/sec.

In order for the last amplifier stage (45 in FIG. 4) to produce this amount of flow, the preceding amplification stages have to amplify the residual sound pressure by a factor of about 10 to about 1,000, and most typically a factor in the range about 50 to about 500. Each amplification stage increases the sound pressure by a factor of about 4 to about 25, depending on local feedback in the amplifier, as will be discussed below. The thickness of the fluidic element construct may typically vary between 1 mm and 5 mm, but other thicknesses may also be useful in specific applications. The number of sheets making up the construct will typically vary between 10 and about 50. The unit stack of the construct would be an approximately square area, with a side of 3 mm to 100 mm, or most typically, from about 5 mm to about 50 mm. The smaller the side of the unit area, the greater the high frequency limit of performance of the construct. A construct with parameters like these would be able to attenuate sound waves in the frequency range about 0.1 Hz to about 2,000 Hz, and most typically in the range about 1 Hz to about 400 Hz.

Figure 5:
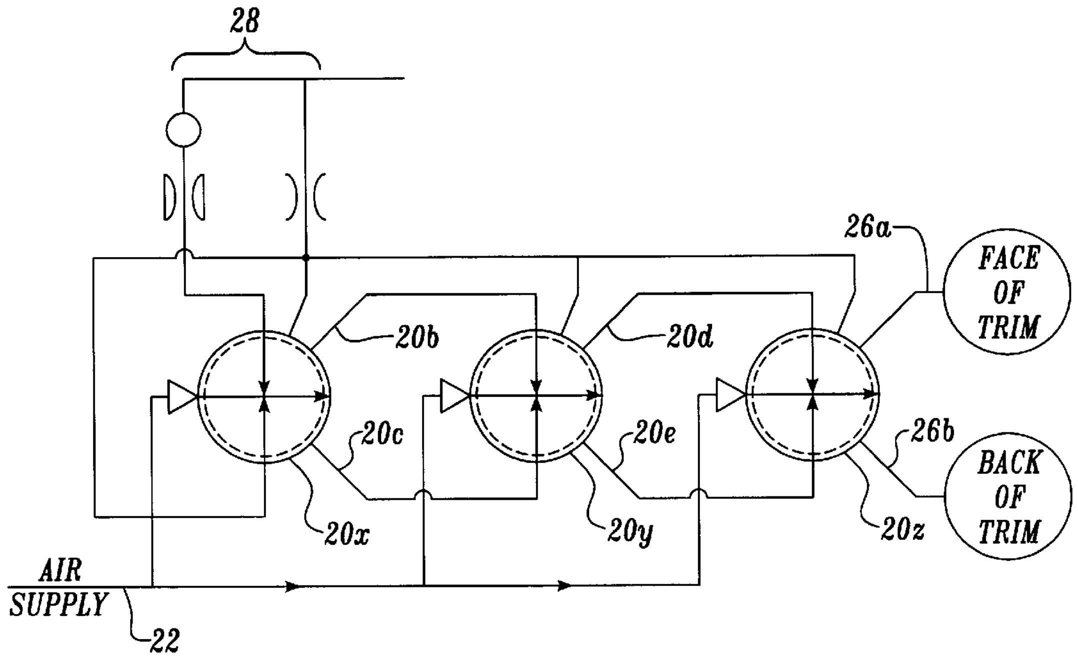
FIG. 5 is a representation of a series of three cascaded fluidic elements of the invention in a fluidic circuit.

FIG. 5 is a schematic representation of a plurality of series of cascaded fluidic elements, such as those illustrated in FIG. 2. As shown, each of the fluidic amplifiers 20*x*, 20*y*, and 20*z* have an input supply of fluid 22, two control ports, and two output ports. Following the diagram from left to right, the outputs 20*b* and 20*c* from the first amplifier 20*x* are amplified in the second amplifier 20*y*, and its outputs 20*d* and 20*e* are in turn further amplified in the third amplifier 20*z*. Clearly, many more than three amplifiers may be cascaded, depending upon the specific application. As before, the acoustically amplified output 26*a* (or "speaker") from the third (last) amplifier 20*z* is exposed to the environment where noise must be reduced, for example the interior of an aircraft. The environment is also connected to one control port of amplifier stage 20*x* (equivalent to the microphone port of FIG. 4). The other output 26*b* is directed away from the zone of interaction between the amplifier output and the environment, and is preferably dumped at a distance from the interaction zone to minimize interference with the output from 26*a*. As is evident to those versed in the art of designing fluidic amplifier circuits, elements of resistance and volume (shown as 28) may have to be added at various points in the circuit in order to achieve pressure biases necessary for all amplifier stages to operate within the linear range.

Figure 6:
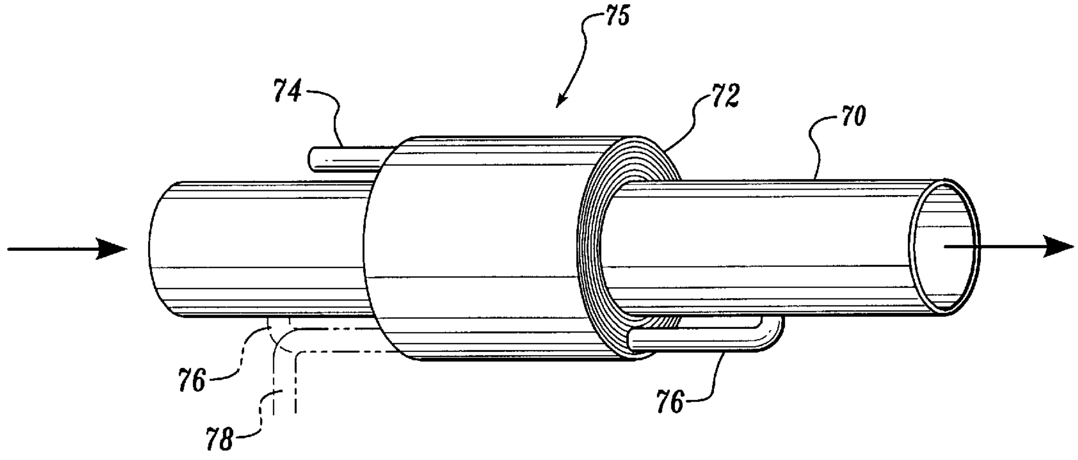
FIG. 6 is a perspective view illustrating an embodiment of a cylindrical muffler that includes a cylindrical fluidic construct in its central portion, in accordance with the invention.

FIG. 6 is a schematic illustration of a further embodiment of the noise reduction constructs of the invention. This construct represents a muffler 75, in which the array of fluidic stacks is arranged in a cylindrical rather than an essentially planar shape. As shown, the construct includes a tubular body 70 surrounded by a cylindrically coiled array of fluidic element stacks 72, located around the mid-section of the tube 70. As before, the fluidic elements include a plurality of cascaded amplifiers for amplifying the acoustic pressure at the construct surface within tube 70. Pressurized fluid is supplied to the construct through tube 74. This supplied fluid is modulated acoustically by the pressure in tube 70, and the resulting countersound again emerges into tube 70, to cause sound attenuation. The unwanted sound from the final amplifier output port is dumped into tube 76, which leads that sound, and the accompanying steady flow, back into the central tube 70. Tube 74 may join tube 70 either upstream of the fluidic array or downstream (shown in broken lines), as shown in FIG. 6. Alternatively, the unwanted sound may be dumped in tube 78 to a remote location.

The fluidic arrays may consist of a planar array which has been bent into a cylindrical shape, or may consist of stacks formed by continuous sheets of fluidic elements wound around a central tube 70. The fluidic elements of the stack arrays, cylindrical or essentially planer, may be complemented by purely passive sound-absorbing elements in order to effect the stability of the active fluidic circuit and to increase the frequency range of attenuation beyond the frequency range of the fluidic array by itself. An example of such a design will be shown among the examples discussed below.

The invention also provides methods of attenuating sound waves in an environment, methods of reducing sound radiation from a vibrating object into an environment surrounding the object, methods of reducing sound-induced vibration of an object in a noisy environment, and methods of absorbing sound waves that would otherwise be incident on an object. The latter methods of absorbing sound include the steps of interposing a fluidic construct of the invention between the sound waves and the object to be protected from sound waves. Pressurized fluid is continuously supplied to supply ports of the fluidic construct. Simultaneously, sound pressure of sound waves to be absorbed is continually sensed at input ports of the construct. Thus, the sensed sound pressure is continuously modulated to generate sound waves that are out of phase with the sensed sound waves, i.e., countersound waves. The fluidic construct continuously outputs a sufficient quantum of fluid having countersound waves in the vicinity of the object being protected from sound waves in the environment, to substantially reduce the sound pressure in the environment and thereby the pressure of these sound waves on the object.

In order to reduce sound radiation from a vibrating object, a similar procedure is followed, except that the continuous countersound output from the fluidic construct of the invention is in the vicinity of the vibrating object and essentially cancels out the sound radiation from the vibrating object. Thus, there is a substantial reduction of noise transmission from the vibrating object into its surrounding environment. Likewise, sound-induced vibration of an object may be reduced by continuously outputting a sufficient volume of amplified fluid from output ports of a fluidic construct according to the invention, in a location adjacent to the surfaces of the object that would otherwise be exposed to the noisy environment. This reduction in sound in the environment able to impact upon the object causes significant reduction in sound-induced vibration excitation of the object.

Thus, the invention provides not only fluidic constructs in a wide range of geometries suitable for specific applications to reduce noise, but also to reduce sound-induced vibration of objects, radiation of sound from objects into an environment, and for absorbing sound waves that might otherwise impact on an object. In addition, the fluidic constructs of the invention offer, for the first time, the capability of controlling broad wave band sound over a wide range of frequencies, ranging from about 0 to about 2,000 Hz. The control of such broad band sound, or noise, is generally regarded as not feasible with the use of electronic microphone and speaker systems, which would require literally thousands of such devices.

The following examples illustrate specific embodiments of the invention, as described above and claimed herebelow. These examples are for illustrative purposes, and to facilitate understanding of the invention, and do not limit the scope of the invention.

EXAMPLES

The individual components of a fluidic amplifier circuit may be modeled with groups of standard components that are used in conjunction with the EASY5 (Engineering Analysis System 5) software that is provided by The Boeing Company of Seattle, Washington. A simulation using this software yielded the following observations and results which may provide useful guidelines to design low-impedance constructs of the invention for specific applications. Clearly, however, the invention is not limited to, or by, the following simulation examples. The examples illustrate conventional transfer function analysis of the open loop (for stability) and the closed loop) (for performance).

The first application is a trim panel, such as may be used in a jet aircraft, that has low radiation efficiency. The panel is designed to have an impedance of the order, or smaller than, the characteristic impedance ρc of the medium into which it radiates. If the panel impedance is 1 ρc, then the noise from a vibrating panel will be from about 6 to about 10 decibels lower than that from a hard panel, depending upon whether the radiation is primarily in the form of plane waves normal to the panel, or in a diffuse field in all directions from the panel.

The second application is a duct muffler, for example, an auxiliary power unit exhaust, or an air-conditioning duct. In general, in jet aircraft low-frequency air conditioner noise is generated in the forced, turbulent mixing of compressed air from the engines outside air, and recirculated cabin air. The amount of attenuation cannot be directly calculated by the use of the EASY5 software, but the impedance output from this program can be used to predict performance using existing duct-acoustic programs.

Figure 7:
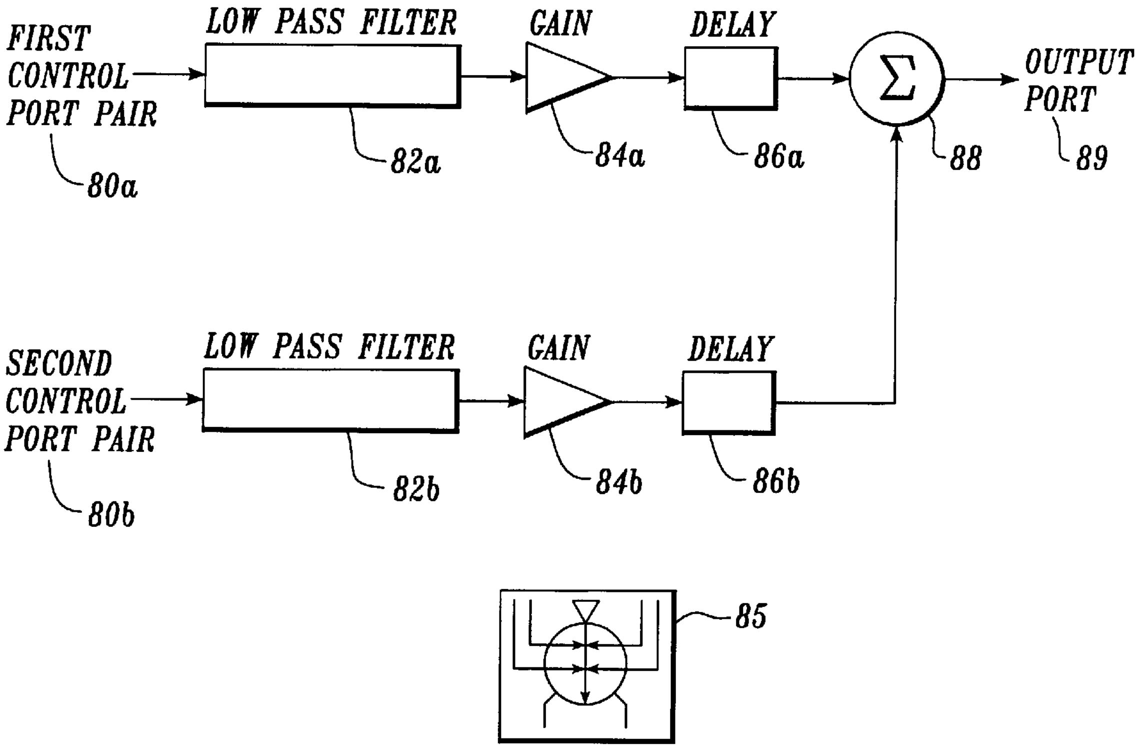
FIG. 7 is a schematic representation of a model of a pressure-amplification stage using the EASY5 model in accordance with the invention.

The basic amplifier model selected is shown in FIG. 7, although other models may also be useful in certain applications. A summing amplifier 85 was selected in order to allow an additional feedback path within the stage to boost the gain, as discussed below. Pressure amplification through gains 84*a* and 84*b* respectively were assumed to be a factor of four, from the first control port 80*a* and a factor of three from the second control port 80*b*. Corresponding time delays 86*a* and 86*b* were assumed to be 0.07, and 0.06 milliseconds, respectively. The time delays were modeled with an 8th order Padé approximation, i.e., the ratio of two 8-order polynomials in the s-plane with unit magnitude. This provides a good linear approximation of the phase over the entire frequency range of interest (0 to 1,000 Hz). The Outputs were summed in 88 for output 89.

There are also input and output impedances, as well as small volumes at each port, that introduce phase lags, to consider. These were modeled as first order low pass filters 82*a, b*, with unit gain in the pass band, and a variable time constant. The filters were combined into a single filter at the control port. While there is a minimum time constant set by the volumes and the impedances, a larger constant may be selected if filtering for circuit stability is desired, by adding to the resistance by use of smaller orifices or adding to the volumes.

Figure 8:
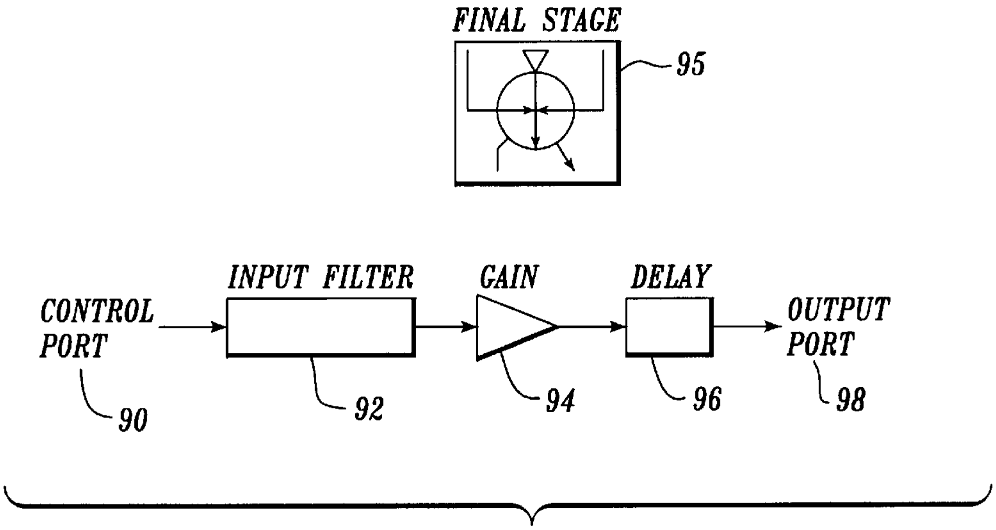
FIG. 8 is a schematic representation of an embodiment of a final stage fluidic amplifier in accordance with the invention, using the EASY5 model.

A final stage amplifier, as modeled, is shown in FIG. 8, with the EASY 5 symbol 95 shown above the connection of the circuit elements. Here a pressure-amplification factor is not appropriate due to the small output load impedance. As can be seen, in this case an amplifier with a single control port pair was selected, since pressure feedback was not practical. The signal from the control port 90 is filtered through input filter 92, amplified in gain 94, and time delayed in delay 96 to produce an output to output port 98.

Figure 9A:
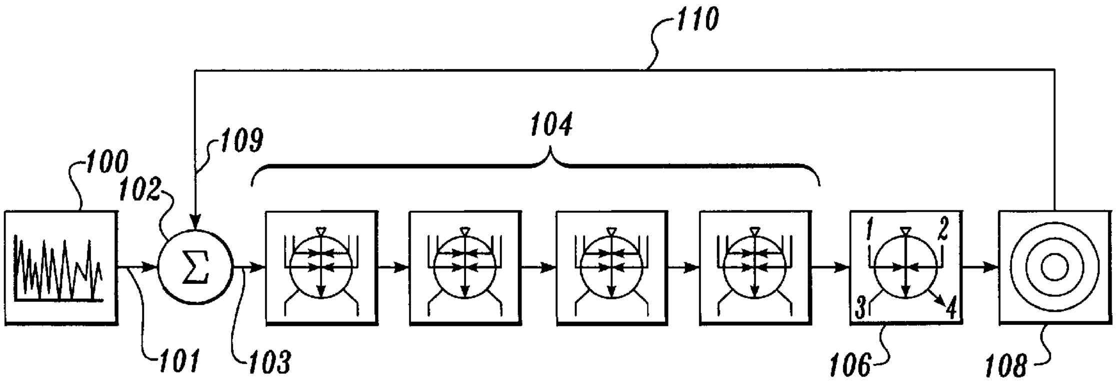
FIG. 9A is a schematic representation of an embodiment of a trim-panel fluidic construct, in accordance with the invention, using the EASY5 model.

A connected five-stage system is shown in FIG. 9A. This circuit is appropriate for analysis of an aircraft interior trim systems performance. The sound from the primary source 100 is mixed at the microphone port 102 with the counternoise from the counternoise output of the circuit via the feedback 110, through the acoustic space at the trim surface. The residual noise is fed through the four pressure amplification stages 104 (of type shown in FIG. 7), and then to the flow amplification stage 106 (of type shown in FIG. 8) to emerge into the environment, symbolized with the radiation impedance 108, which has been assumed to be 1 ρc. It has been assumed that the output load impedance on amplifier 106 is negligible. The signal from this output is delayed by the propagation time from the loudspeaker port to the microphone port, which are assumed to be 0.01 meters apart. The open loop gain is measured from the summing-junction 102 output 103 to the top input 109 of the same summing junction; and the closed loop performance is measured from the left input 101 of the summing junction to its output 103.

Figure 9B:
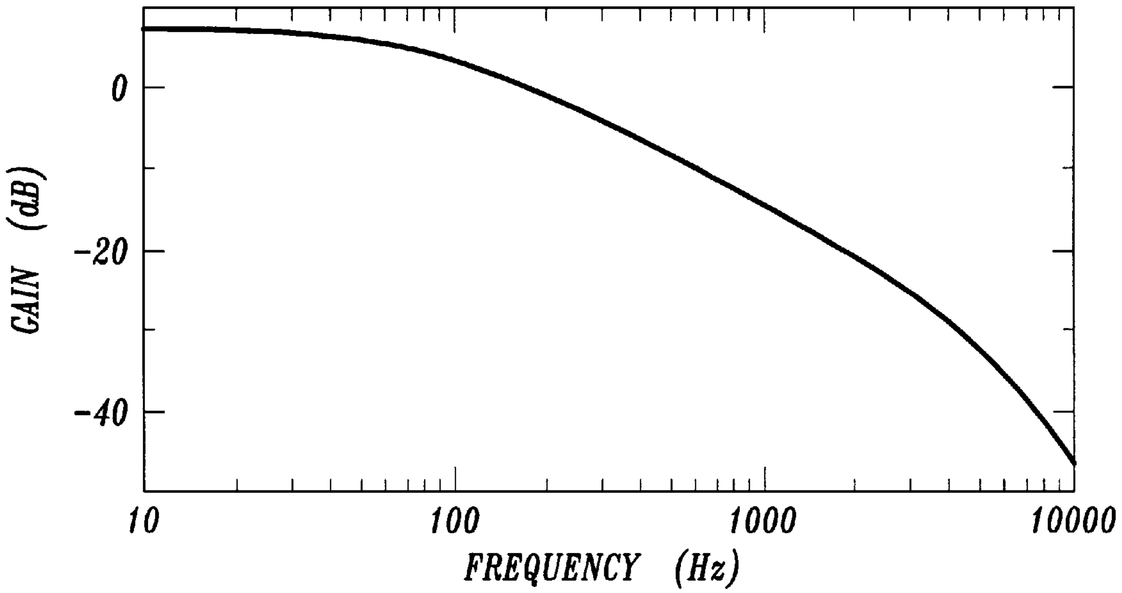
FIG. 9B is a graphical depiction of open loop gain and phase vs. frequency for the model of FIG. 9A.
Figure 9C:
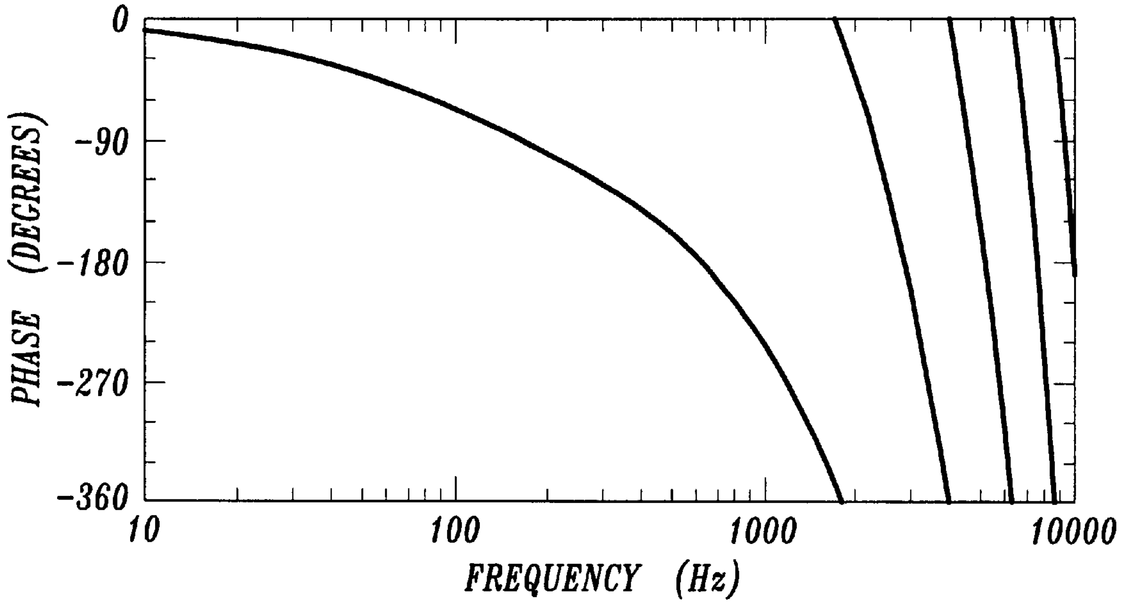
FIG. 9C is a graphical depiction of phase vs. frequency for the model of FIG. 9A.

The open loop gain is shown in FIG. 9B. The component parameters have been adjusted such that there is 10 dB gain margin where the phase around the loop is 180°. The phase margin at zero loop gain is 90°. The corresponding closed loop performance is shown in FIG. 9C. The component parameters assumed to achieve this performance are as follows: for each pressure amplification stage in assembly 104, an amplification by a factor of 4, time delay 0.07 ms, and low pass corner frequency of 10,000 Hz. For the flow-amplification stage 106 in FIG. 9A, a transfer admittance of $3.2\times10^{-8}$ cubic meters per second per newtons per meter square, time delay 0.07 milliseconds, and a low pass corner frequency of 80 Hz have been assumed. Somewhat better performance in the attenuation band could be obtained with smaller margins, but then the out-of-band amplification would be greater.

A method for reducing the number of fluidic amplifier elements in the stack circuit is explained below. Such a design lead to a thinner stack and may therefore reduce the bulk, weight and cost of the construct. By adding a positive feedback loop around each pressure amplifier the gain may be stably boosted, as long as the loop gain is less than 1. In FIG. 10 the amplifier 112 has a gain of $F_1$ from input 111*a* to output 114 and a gain $F_2$ from input 111*b* to output 114, without feedback impedances $Z_1$ (116) and $Z_2$ (118) connected. With $Z_1$ and $Z_2$ (typically resistive orifices) connected, part of pressure $P_2$ at output port 114 is sensed at input port 111*b*. This part is $\beta=Z_1/(Z_1+Z_2)$. The pressure $P_2$ at output 114 will therefore be a sum of the pressure $P_1$ at input port 111*a* amplified by gain $F_1$ and the fed back pressure at input port 111*b*, amplified by gain $F_2$. Therefore, $P_2=F_1P_1+\beta F_2P_2$ or $P_2=(F_1/(1-\beta F_2))P_1$. Without feedback, the relation would be $P_2=F_1P_1$. With the arrangement shown in FIG. 10 gain is thus boosted by a factor of $1/(1-\beta F_2)$. The time delay associated with the travel distances and the capacitances associated with the volumes of the feedback loop must be considered in calculating $Z_1$ and $Z_2$, but as long as $\beta F_2$ is not equal to 1, the circuit is stable.

In the EASY5 modeling of the feedback, illustrated in FIG. 10, it was assumed that the feedback is made to the second control port pair 80*b* in FIG. 7 which has a smaller gain 3. $Z_1$ is the second control port input impedance, and $Z_2$ is an appropriate orifice resistance.

It should be appreciated that variations in the performance of the fluidic circuits can be accomplished by appropriate filtering at the amplifier inputs. If band pass filtering is used, instead of low pass filtering, the frequency region of useful performance can be extended upward, at the expense of some low-frequency performance drop. The realization of such filters using resistive and volumetric elements are apparent to those versed in the art of acoustic filtering.

Figure 11A:
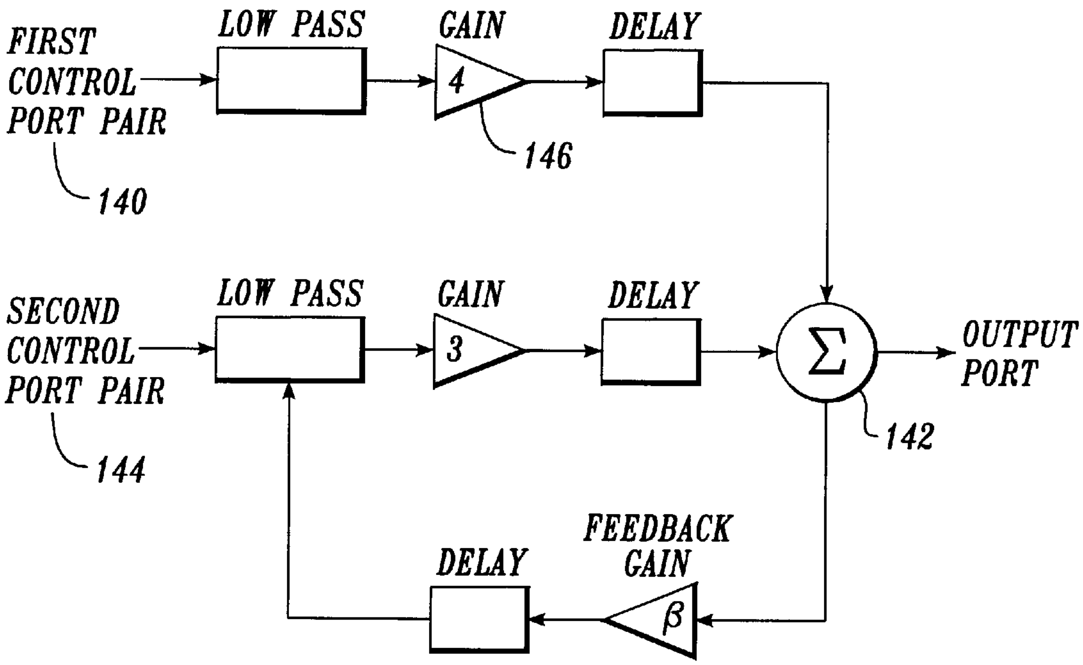
FIG. 11A is a schematic representation of an embodiment of a pressure-amplification stage, with feedback boost in accordance with the invention, using the EASY5 model.

FIG. 11A illustrates schematically a pressure-amplification stage with feedback boost. Essentially, FIG. 11A is a combination of the circuit shown in FIG. 7 and the circuit of FIG. 10, with an associated delay in the feedback loop. The benefits of such a system include a thinner construct due to fewer fluidic elements in the stack but they are bought at a reduce high-frequency performance of the circuit.

Figure 11B:
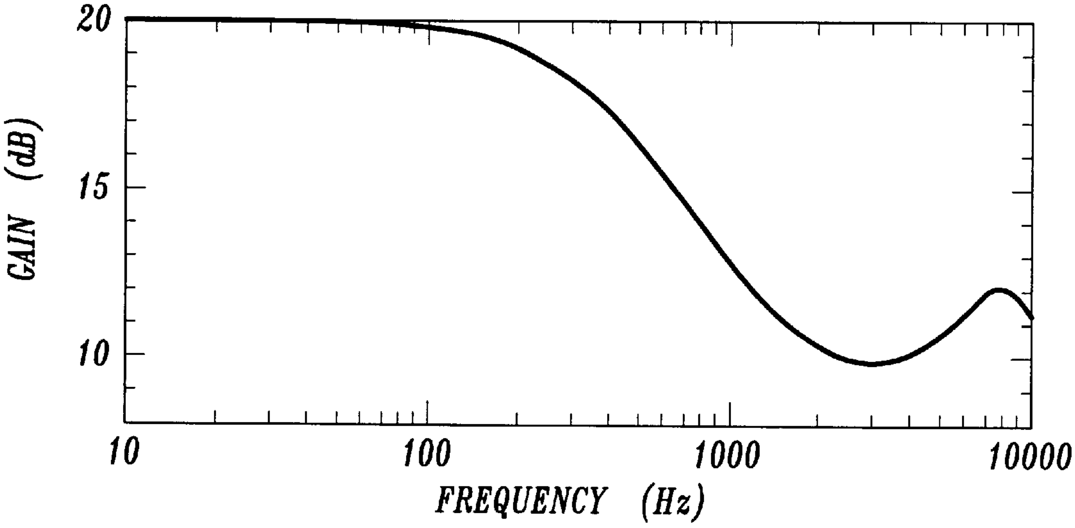
FIG. 11B is a graphical representation of the performance characteristics of the model of FIG. 11A.

FIG. 11B is a graphical representation of the output of the circuit of FIG. 11A. FIG. 11B clearly shows that the gain from first control port 140 to output port 142 is greater (20 dB) than it would be without the feedback via second control port 144, in which case it would be a factor of 4 (12 dB) of gain block 146. Due to the time delays in the circuit, the gain boost persists only up to a few hundred Hz.

Figure 12A:
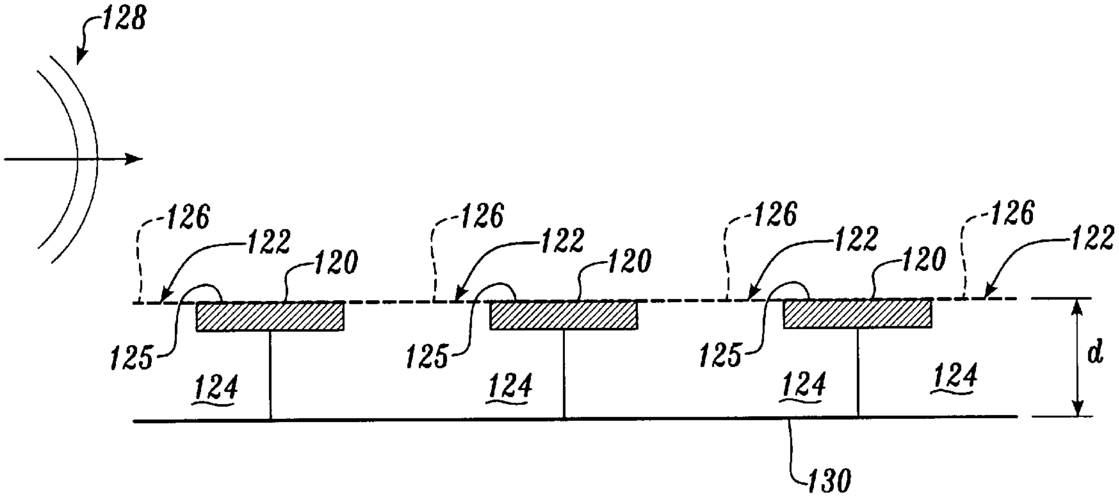
FIG. 12A is an illustrative embodiment of an active air-conditioning muffler lining, in accordance with the invention.
Figure 12B:
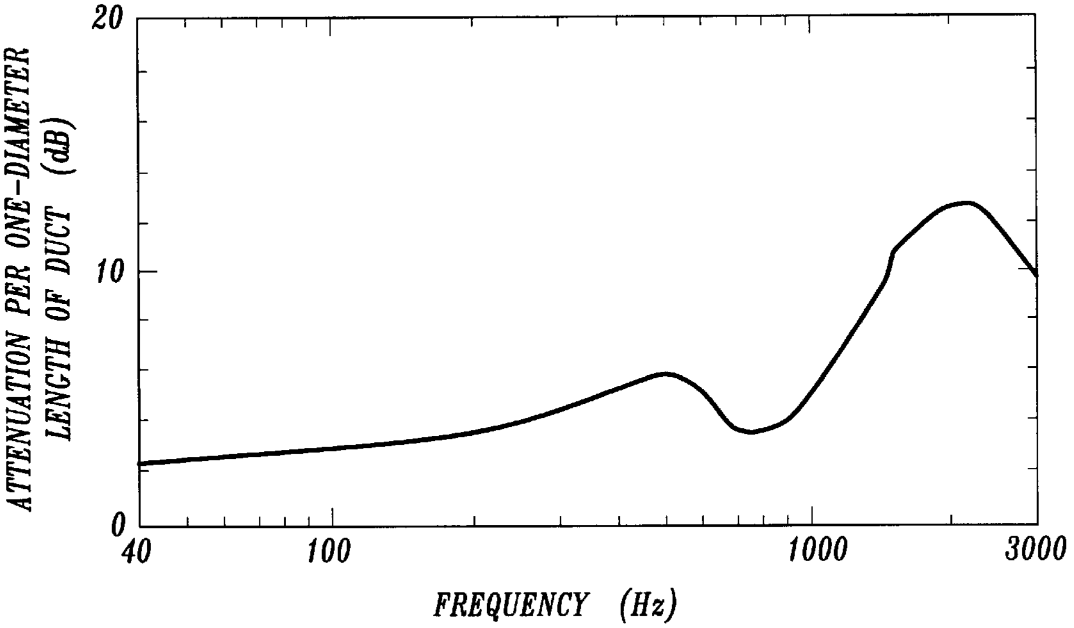
FIG. 12B is a graphical representation of the performance characteristics of the muffler of FIG. 12A.

FIG. 12A illustrates a simplified schematic of a muffler lining where active 120 and passive 122 lining elements have been combined, and its corresponding acoustic performance is shown in FIG. 12B. The passive lining 122 has a two-fold purpose. Firstly, it provides damping of the feedback from the active lining microphone ports to its loudspeaker ports. Secondly, it provides attenuation at frequencies above the attenuation band of the active lining.

The active lining elements 120 shown in FIG. 12A occupy about one-half of the total lining surface and face the sound waves 128 to be controlled. The active lining elements 120 consist of stacks of fluidic elements substantially with the configuration shown in FIG. 9, except that only two pressure amplification stages are used. Each of these stages has the configuration shown in FIG. 11A. In addition, the face plate 125 of the stack is covered with a resistive sheet of impedance 4 ρc. It is understood that this resistance is averaged over the whole stack area, i.e., if the loudspeaker ports occupy five percent of the total stack area, then the resistance in front of the loudspeaker ports is 5% of 4 ρc.

The passive part 122 of the lining consists of a resistive face of sheet 126 of impedance 1 ρc, over an array of cavities 124 of depth d of about one inch, that space the passive and active elements from the muffler housing 130. Note that the cavities occupy the space under the 1 ρc base sheet 126, as well as the space under the active lining elements 120, which have been assumed to be 0.25 inches deep.

The performance graph FIG. 12B gives an estimate of the attenuation of the configuration of FIG. 12A per unit length, equal to one diameter of the duct in an air conditioning muffler. The muffler was assumed to have a cross section with internal diameter of 11 inches.

While the preferred embodiments of the invention have been illustrated and described, it will be appreciated that various changes can be made therein without departing from the spirit and scope of the invention as described above and claimed hereafter.

The embodiments of the invention in which an exclusive property or privilege is claimed are defined as follows:

1. A construct for attenuating sound waves in a fluid environment, the construct comprising:

(a) a face plate having a plurality of pairs of input and output ports in fluid communication with the fluid environment, each input port of a pair being proximate to the corresponding output port of the pair;

(b) a stack of fluidic laminae, each fluidic lamina including a plurality of fluidic elements, said fluid elements including fluidic transfer elements and fluidic amplifiers, the fluidic elements included in a fluidic lamina being in fluid communication with fluidic elements in adjacent fluidic laminae to form a plurality of interconnected fluidic elements, the fluidic lamina located on one surface of the stack of fluidic laminae being juxtaposed against the face plate, the pairs of input ports and output ports of the face plate being oriented such that the input ports and output ports are in fluid communication with an associated one of said plurality of interconnected fluidic elements; and (c) a back plate having a plurality of fluid supply ports, dump ports and vent ports, the back plate being juxtaposed against the fluidic laminae layer remote from the face plate, the supply ports, dump ports, and vent ports being oriented such that the supply ports, dump ports, and vent ports are in fluid communication with the fluidic elements, the fluidic elements, the input ports, the output ports, the dump ports and the vent ports being arranged such that the supply ports receive a pressurized fluid, the dump ports provide outlets for a residual sound wave out of phase with an outgoing sound wave emanating from the output ports, and the vent ports open to ambient pressure, so that an incoming sound wave entering an input port is counteracted by the outgoing sound wave emanating from the corresponding output port of the pair of input and output ports, the outgoing sound wave being out of phase with the incoming sound wave.

2. The construct of claim 1, wherein each fluidic lamina has a thickness from about 0.1 mm to 1 mm.

3. The construct of claim 2, wherein the fluidic transfer elements have orifices and volumes for acoustically filtering a fluid flowing through the fluidic elements to prevent the occurrence of self-excited oscillations.

4. The construct of claim 1, wherein the fluidic transfer elements have orifices and volumes for acoustically filtering a fluid flowing through the fluidic elements to prevent the occurrence of self-excited oscillations.

5. The construct of claim 1, wherein the face plate forms the interior surface of a chamber, the face plate facing the interior of the chamber.

6. The construct of claim 5, wherein the chamber is the fuselage of an aircraft.

7. The construct of claim 5, where the chamber is a room and the face plate forms a wall surface of the room.

8. The construct of claim 5, wherein the chamber is a muffler.

9. The construct of claim 8, wherein the muffler has a cylindrical shape.

10. A method of attenuating sound waves in a fluid environment, the method comprising:

(a) receiving at a plurality of input ports sound waves to be attenuated, each input port located proximate to a corresponding output port, said input ports and corresponding output ports are located in a face plate;

(b) supplying the sound waves to be attenuated received at each of the plurality of input ports to a corresponding stack of fluidic elements for amplitude and phase modulating a pressurized fluid supplied to the stacks of fluidic elements to produce modulated pressurized fluid that is out of phase with the sound waves received at the corresponding input ports, said stacks of fluidic elements including fluidic amplifiers, the fluidic elements included in a stack of fluid laminae such that the fluidic elements in adjacent laminae are interconnected, the plurality of input ports being located on one surface of said stack of fluid laminae;

(c) conducting the out-of-phase modulated pressurized fluid produced by said stacks of fluidic elements to corresponding output ports; and (d) eliminating interference between the out-of-phase modulated pressurized fluid conducted to the corresponding output port and a residual portion of the pressurized fluid supplied to the stacks of fluidic elements.

11. The method of claim 10, further comprising filtering the out-of-phase modulated pressurized fluid supplied to the output ports to reduce self-excited oscillations.

12. A method of attenuating sound waves radiating from a vibrating object into an environment surrounding the object, the method comprising:

(a) interposing between the vibrating object and the environment surrounding the vibrating object an array of stacks of fluidic elements;

(b) receiving at a plurality of input ports sound waves to be attenuated, each input port located proximate to a corresponding output port, said input ports and corresponding output ports are located in a face plate;

(c) supplying the sound waves to be attenuated received at each of the plurality of input ports to a corresponding stack of fluidic elements for amplitude and phase modulating a pressurized fluid supplied to the stacks of fluidic elements to produce modulated pressurized fluid that is out of phase with the sound waves received at the corresponding input port, said stacks of fluidic elements including fluidic amplifiers, the fluidic elements included in a stack of fluid laminae such that the fluidic elements in adjacent laminae are interconnected, the plurality of input ports being located on one surface of said stack of fluid laminae;

(d) conducting the out-of-phase modulated pressurized fluid produced by each of the stacks of fluidic elements to the output port corresponding to the input port supplying sound waves to be attenuated to the stack of fluidic elements; and (e) eliminating interference between the out-of-phase modulated pressurized fluid conducted to the corresponding output ports and a residual portion of the pressurized fluid supplied to the stacks of fluidic elements.

13. The method of claim 12, further comprising filtering the out-of-phase modulated fluid conducted to the output ports to reduce self-excited oscillations.

* * * * *